(12) United States Patent
Nakano et al.

(10) Patent No.: US 6,439,026 B2
(45) Date of Patent: Aug. 27, 2002

(54) ODOR MEASURING APPARATUS

(75) Inventors: Hiroshi Nakano, Kyotanabe; Junichi Kita, Kyoto, both of (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/887,100

(22) Filed: Jun. 25, 2001

(30) Foreign Application Priority Data

Jul. 3, 2000 (JP) ........................ 2000-200753

(51) Int. Cl.$^7$ .................... G01N 33/497; G01N 27/00
(52) U.S. Cl. ............................... 73/23.34; 422/98
(58) Field of Search .................... 73/23.34, 31.06; 422/88, 98, 96; 338/34

(56) References Cited

U.S. PATENT DOCUMENTS 3,815,405 A * 6/1974 Dravnieks .............. 73/23.34
5,047,214 A * 9/1991 Fukui et al. ............. 422/98

FOREIGN PATENT DOCUMENTS

JP 1121851 * 8/1999 .......... G01N/27/12

* cited by examiner

Primary Examiner—Hezron Williams
Assistant Examiner—J L Politzer
(74) Attorney, Agent, or Firm—Kanesaka & Takeuchi

(57) ABSTRACT

In an odor measuring apparatus, a plurality of detection outputs with respect to a sample gas is obtained by a plurality of odor sensors having different response characteristics. In an odor fractionation processing section, based on the detection outputs, it is determined which one of a plurality of predetermined odor categories the odor of the sample gas belongs to. In case of calculating an odor index from the detection outputs, the same regression line can be utilized for the same odor category. An odor index calculating section utilizes regression coefficients determined in advance for each odor category, to thereby calculate the odor index. Accordingly, without using an organoleptic test by panels, the odor index can be obtained easily and accurately.

8 Claims, 3 Drawing Sheets

ODOR MEASURING APPARATUS

BACKGROUND OF THE INVENTION AND RELATED ART STATEMENT

The present invention relates to an odor measuring apparatus which measures odor components contained in a sample gas, and more particularly, it relates to an odor measuring apparatus for indicating a degree of odor in an index value, such as an odor index and an odor intensity. An odor measuring apparatus according to the present invention can be used in a wide range of fields, such as quality inspection for food or perfume, quantitative detection of malodor pollution, fire alarm by a scorched or burnt odor, and criminal investigations including tracking, identification, and authentication of a person, or drug test.

Conventionally, in order to find an odor index or odor intensity that is so-called organoleptic or sensitive intensity value, a sensory test in which a human's olfaction or sense of smell is actually used. The method of the test as described above is defined in, for example, "METHOD OF CALCULATING AN ODOR INDEX" in Notification No. 7 (1996) of the Environment Agency in Japan. Also, regarding substances, such as twenty-two kinds of substances (for example, hydrogen sulfide, formaldehyde) causing malodor which have been already defined in a "AKUSHU BOSHI HO (Malodor Prevention Law in Japan)", in which correlation between a concentration of a substance and an odor index or odor intensity is known, the concentration of the substance is measured by an instrumental analysis using an analyzer, such as a gas chromatography, and the concentration is converted into the odor index or the odor intensity.

Although the sensory test described above has been used widely heretofore, since a person's olfaction is utilized, it has to be understood that a sense of smell changes in accordance with an individual difference and a daily condition of a person who smells an odor (hereinafter referred to as a panel). Therefore, in order to obtain an objective result accurately, it is necessary to use a predetermined number of panels or more, and an environment of a test site or the like must be considered well. Thus, it requires a large amount of labor and time therefor.

On the other hand, in the odor analysis utilizing the analyzer, the odor index or odor intensity can be calculated regarding a limited, single substance as described above. However, in reality, most of odors exhausted by industrial activities are compound odors in which a plurality of substances is mixed, and the conventional odor analysis utilizing the analyzer has a disadvantage that the odor index of the compound odor can not be computed.

The present invention has been made in view of the foregoing, and an object of the invention is to provide an odor measuring apparatus which can easily and accurately find an index value of odor that was obtained by the organoleptic test by a panel conventionally.

Further objects and advantages of the invention will be apparent from the following description of the invention.

SUMMARY OF THE INVENTION

To achieve the above object, the present invention provides an odor measuring apparatus, which is formed of a plurality of detecting means having different characteristics to detect odor components in a sample gas; odor fractionating means for determining which one of odor categories an odor in the sample gas belongs to based on a plurality of detection outputs obtained from the detecting means; and computing means for calculating an index value regarding the odor based on the detection outputs obtained from the detecting means by using a regression line determined in advance for each of the odor categories.

As the detecting means, there can be effectively used so-called odor sensors, which electrically or optically measures physical changes of the sensors occurring when odor components contained in air or the supplied sample gas adhere to sensitive films of the sensors. As the odor sensors, there are sensors using oxide semiconductors, or sensors using conductive high polymers.

In particular, the odor measuring apparatus of the invention includes a plurality of different kinds of odor sensors which are different in structures, or materials for sensitive films, and by exposing the odor sensors in a sample gas, a plurality of detection outputs is obtained. The odor fractionation means uses the plurality of detection outputs, and fractionates the odor of the sample gas into one of the odor categories or ranges. Here, the odor categories mean classification of sensuous odors, such as a burnt odor and a rotten odor, irrespective of the materials contained in the sample gas. In order to fractionate these kinds of the odors, for example, there can be used various kinds of methods, such as a method of determining a similarity of combination patterns of the plurality of detection outputs, a method of using various techniques of multivariate analyses, that is, a cluster analysis and a principal component analysis, and a method of using a neural network.

Then, the computing means calculates an index value, such as an odor index or odor intensity, by a regression analysis method based on the plurality of the detection outputs. At this time, information regarding the odor categories, i.e. qualities of the odors, obtained before is utilized. According to the experiments by the inventors of the present invention, as long as the appropriate odor categories are set, even if contents or substances are different, the same regression line can be utilized for each odor category in order to compute the index value, such as the odor index. Namely, a regression coefficient can be determined in advance for each category of the odor, and at the time of measuring the odor, the index value is computed from the regression coefficient and the plurality of the detection outputs.

DETAILED DESCRIPTION OF PREFERRED EMBODIMENTS

Figure 1:
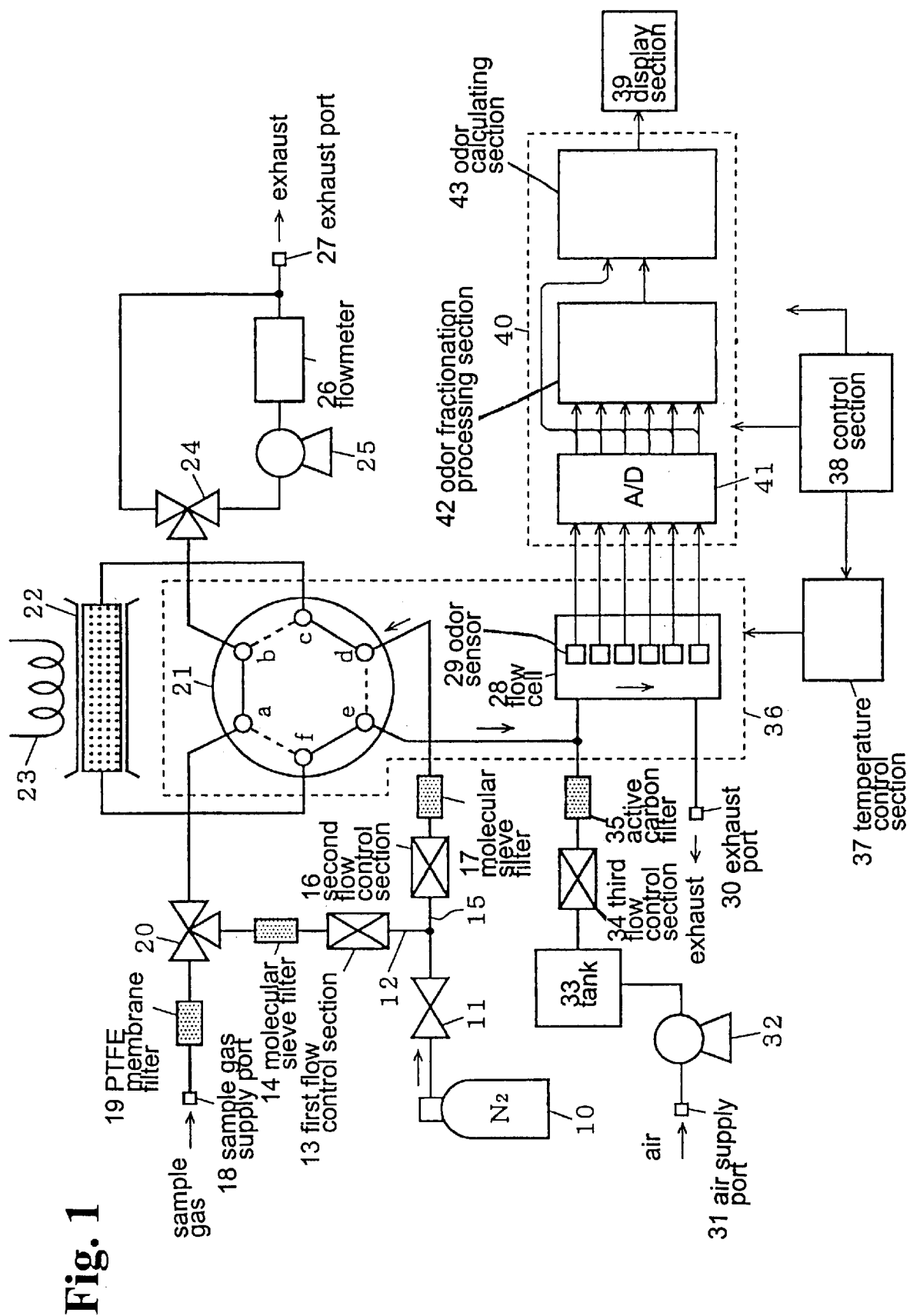
FIG. 1 is a structural diagram showing an odor measuring apparatus as an embodiment of the invention.

Hereinafter, an embodiment of the odor measuring apparatus according to the present invention will be explained with reference to the attached drawings. FIG. 1 is a structural diagram of the odor measuring apparatus, which is shown on the basis of gas passages.

In FIG. 1, a gas outlet of a nitrogen gas container 10 filled with pure nitrogen gas ($N_2$) is attached to a constant pressure valve 11, and an outlet of the valve 11 is branched into first and second passages 12 and 15. Namely, the first nitrogen gas passage 12 has a first flow control section 13, such as a mass flow controller, and a molecular sieve filter 14 for removing impurities, and the second nitrogen gas passage 15 has a second flow control section 16, such as a mass flow controller, and a molecular sieve filter 17 for removing impurities. A sample gas passage, which is connected to a sample gas supply port 18 through a PTFE (polytetrafluoroethylene) membrane filter 19 for removing dusts, and the first nitrogen gas passage 12 are selectively connected to a port a of a six-way or hexagonal valve (six-port and two-position valve) 21 through a three-way valve 20. Also, the second nitrogen gas passage 15 is connected to a port d of the six-way valve 21. A collecting tube 22 provided with a heater for heating is connected between a port c and a port f of the six-way valve 21. The collecting tube 22 is filled with, for example, a carbon adsorbent, or other appropriate adsorbent in accordance with the odor components of the measurement object.

The port b of the six-way valve 21 is selectively connected by a three way valve 24 to either a passage passing through a pump 25 and a flowmeter 26 or a passage not passing through these members, and either of the passages leads to an exhaust port 27. A port e of the six-way valve 21 is connected to a flow cell 28 in which a plurality of odor sensors 29 (six odor sensors in the embodiment) is disposed, and a downstream side outlet of the flow cell 28 is connected to an exhaust port 30. The odor sensors 29 are sensors using metal oxide semiconductors as sensitive films, which have characteristics different in detection sensitivities with respect to various kinds of odor components, respectively. The six-way valve 21 and the flow cell 28 are disposed inside a thermostat tank 36, a temperature of which is controllable at a predetermined temperature by a temperature control section 37.

In a tank 33, air sucked from an air supply port 31 by a pump 32 is compressed and stored, and an outlet of the tank 33 is connected to an inlet of the flow cell 28 through a third flow control section 34 and an active carbon filter 35 for removing impurities. Accordingly, an adequate amount of air can be mixed with a sample gas flowing into the flow cell 28. Incidentally, it can be structured that a pure oxygen gas may be mixed instead of air. If the pure oxygen gas is used, a volume thereof mixing with the sample gas can be extremely reduced as compared with the case using air, so that the ratio of diluting the odor components is small to be advantageous in improving the sensitivity of the detection by the odor sensor 29.

Detection signals from the six odor sensors 29 are inputted in parallel into a signal processing section 40. The signal processing section 40 includes an analog-to-digital converter 41 for converting an analog detection value of each odor sensor 29 into a digital value, an odor fractionation processing section 42, and an odor index calculating section 43. The odor fractionation,processing section 42 and the odor index calculating section 43 can be made by executing a predetermined software in, for example, a personal computer. The odor index calculated at the signal processing section 40 is displayed at a display section 39. Also, a control section 38 has a function of controlling the three-way valves 20 and 24, the six-way valve 21, the pumps 25 and 32, the heater 23, the temperature control section 37, and the signal processing section 40 or the like as described later in accordance with a predetermined program.

Incidentally, although the metal oxide semiconductor sensors are used as the odor sensors 29 in the present embodiment, the odor sensors 29 are not limited thereto, and sensors utilizing conductive high polymers can be used as the odor sensors 29. In this case, since there is no need to supply air or oxygen to the flow cell 28, in the structure shown in FIG. 1, the structure for mixing air with the gas flowing into the flow cell 28 can be omitted.

Next, operations in case of obtaining the detection signals by the odor sensors 29 in the odor measuring apparatus will be explained.

Collecting Odor Components

Firstly, the control section 38 switches the three-way valve 20 such that the sample gas supply port 18 and the port a of the six-way valve 21 are connected, and at the same time, the control section 38 switches the three-way valve 24 such that the port b of the six-way valve 21 is connected to the pump 25. Also, the six-way valve 21 is switched to become a connection condition shown by broken lines in FIG. 1, and the pump 25 is actuated. Accordingly, a relatively large solid suspended material, such as dust, contained in the sample gas sucked from the sample gas supply port 18 by a suction force of the pump 25 is removed from the sample gas by the membrane filter 19, and the sample gas is introduced into the collecting tube 22 through the three-way valve 20 and the six-way valve 21 (in a left to right direction in FIG. 1). Further, the sample gas passes through the six-way valve 21, the three-way valve 24, the pump 25 and the flowmeter 26, and is discharged from the exhaust port 27. At this time, heating by the heater 23 is not carried out.

When the sample gas passes through the collecting tube 22 as described above, odor components contained in the sample gas are adsorbed by the adsorbent. In the present embodiment, the control section 38 controls the suction force of the pump 25 such that the detection value by the flowmeter 26 becomes a predetermined constant value, and flowing time of the sample gas becomes a predetermined value.

Replacement of the Gas in the Collecting Tube

When the flowing time has elapsed, the control section 38 switches the three-way valve 20 to connect the first nitrogen gas passage 12 with the port a of the six-way valve 21, and at the same time, the control section 38 switches the three-valve 24 to connect the port b of the six-way valve 21 directly with the exhaust port 27. Accordingly, instead of the sample gas, the nitrogen gas supplied from the nitrogen gas container 10 passes through the first nitrogen gas passage 12, the three-way valve 20, the six-way valve 21, the collecting tube 22, the six-way valve 21, and the three-way valve 24, and is discharged from the exhaust port 27. As a result, the sample gas remained in the passages or flowing route including the collecting tube 22 is pushed to an outside by the nitrogen gas. At this time, since the heating by the heater 23 is not carried out, the odor components adsorbed by the adsorbent earlier remain as they are. On the other hand, since the nitrogen gas is extremely dry, most of water adsorbed to the adsorbent and moisture adhering to the inner walls of the passages are vaporized into the nitrogen gas and carried away to the outside, so that dehumidification to the certain extent can be achieved.

Introduction of the Odor Components into the Odor Sensors

After the nitrogen gas flows through the collecting tube 22 for an adequate time, and the control section 38 switches the six-way valve 21 to become a connection condition shown by the solid lines in FIG. 1. Then, there is formed a flowing route comprising the second nitrogen gas passage 15, the six-way valve 21, the collecting tube 22, the six-way valve 21, the flow cell 28, and the exhaust port 30. In this condition, the heater 23 is energized, and the collecting tube 22 is heated rapidly, for example, at the temperature rising speed of approximately 10° C./second. As a result, the odor components adsorbed to the adsorbent in the collecting tube 22 are released from the adsorbent, and are carried to the flow cell 28 by the nitrogen gas flowing in the direction opposite to the direction flowing before, i.e. right to left in FIG. 1.

Air stored in the tank 33 is adjusted to have an adequate flow rate by the third flow control section 34, and after the undesired components causing a disturbance of the measurement is removed by the active carbon filter 35, air is mixed with the measurement gas flowing into the flow cell 28. Since air contains the oxygen gas, the oxygen gas together with the odor components flow into the flow cell 28, and the oxygen gas moleculars are adsorbed by sensitive films formed of metal oxide semiconductors, so that an oxidation reduction reaction occurs between the oxygen gas moleculars and the molecules of the odor components. Accordingly, conductivities of the odor sensors 29 are changed, and electric resistance between electrodes thereof is changed. The detection signals due to the resistance change are sent to the signal processing section 40.

During the measurement as described above, the six-way valve 21, the flow cell 28 and the passage connecting therebetween are maintained at a fixed temperature, for example, about 40° C., which is slightly higher than the room temperature. As a result, the effect to the odor sensors 29 due to the change of the ambient temperature can be decreased, and it can be prevented that the stability of the detection sensitivity is deteriorated due to adhesion of the high boiling compounds to the inner wall of the passages.

Cleaning the Odor Sensors

When the odor components adsorbed to the adsorbent in the collecting tube 22 are sufficiently released, the control section 38 switches the six-way valve 21 again to become the connection condition shown by the broken lines in FIG. 1, and the temperature in the tank 36 is increased by the temperature control section 37 to a predetermined temperature. Accordingly, the clean nitrogen gas flows through the flow cell 28. When the temperatures of the odor sensors 29 rise, the odor components or other impurities adsorbed to the sensitive films of the odor sensors 29 can be easily released, and exhausted from the exhaust port 30 by being carried on the nitrogen gas. As a result, the sensitive films of the odor sensors 29 are recovered, and return to the condition capable of detecting the odor components again.

Figure 2:
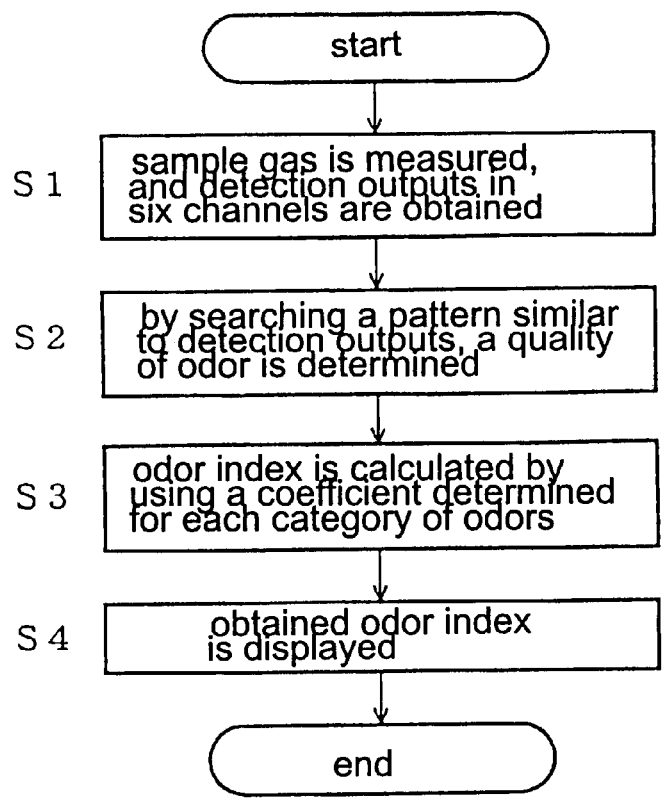
FIG. 2 is a flow chart schematically showing processes in case of calculating an odor index in the odor measuring apparatus.

Next, a method of calculating the odor index in the odor measuring apparatus described above will be explained with reference to a flow chart in FIG. 2.

Firstly, the sample gas is measured as described above, and the detection outputs in six channels are obtained from the six odor sensors 29 (step S1). Since the six odor sensors 29 have different selectivity and response characteristics, respectively, for example, it may happen that with respect to a certain odor component, a large detection output can be obtained from one of the odor sensors, but no detection output is obtained from the rest of the odor sensors.

Figure 3:
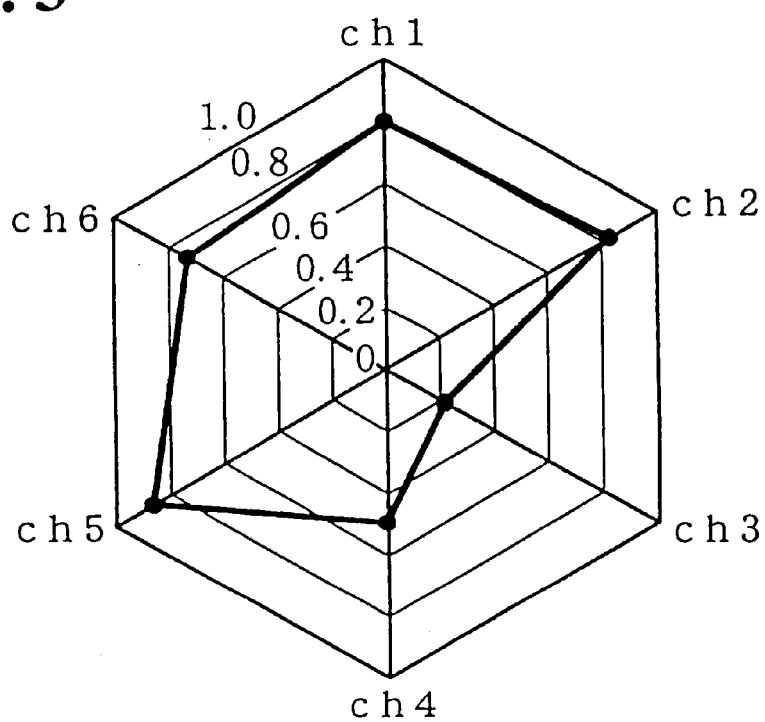
FIG. 3 is a radar graph showing a distribution of detection outputs of respective channels.

FIG. 3 is an example of a radar graph showing a distribution of the detection outputs by the respective channels. Irrespective of the substances causing the odors, a pattern of the radar graph results in a similar one for each of odor categories of a plurality of predetermined odors, such as a burnt odor, a rotten odor, and a musty odor. Thus, the odor categories in the plurality of the odors described above and typical patterns of the radar graphs thereof are obtained by experiments, and stored in a memory built in the odor fractionation processing section 42 of the signal processing section 40.

At the time of measuring the sample gas, the odor fractionation processing section 42 receives the detection outputs of the six channels converted into the digital signals at the analog-to-digital converter 41, and a radar graph like the radar graph described above is formed to see which stored pattern is most similar to the formed radar graph. Then, according to a result thereof, the category of the odor of the sample gas is determined (step S2).

Thereafter, the odor index calculating section 43 calculates an odor index by the regression analysis method by using the fractionation result of the category of the odor and the detection outputs from the six channels (step S3). By conducting many experiments, the inventors of the present invention found that the plurality of detection outputs and the odor index can be expressed by a relation of a liner regression. Namely, in this example, the odor index P can be found by the following formula.

$$P = a \times S1 + b \times S2 + c \times S3 + d \times S4 + e \times S5 + f \times S6 + g$$

Incidentally, Sn is a detection output of a channel of a number n (n=1 through 6), and a through g are coefficients.

Further, it was found that in the above formula, the coefficients a through g can be the same values for the same category of the odor. Namely, as long as the category of the odor is the same, irrespective of the contained components thereof, an odor can be placed on the same regression line. Thus, the coefficients a through g are found in advance by the experiments for each of the categories of the odors, and the coefficients are stored in a memory in the odor index calculating section 43. Then, at the time of measuring the sample gas, the odor index calculating section 43 reads out the coefficients responding to the information regarding the category of the odor inputted from the odor fractionation processing section 42, and calculates the odor index by the aforementioned formula. Then, the display section 39 displays the found odor index (step S4).

Figure 4:
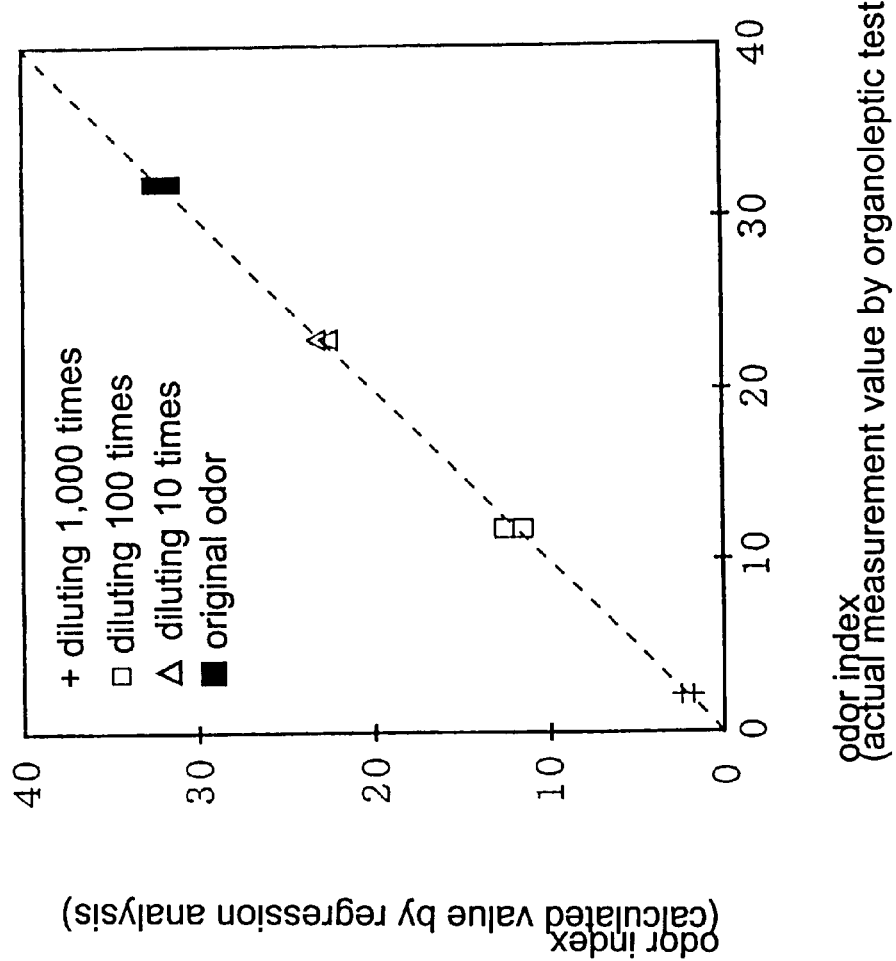
FIG. 4 is a graph showing a correspondence relationship between odor indexes calculated by a method of the invention and odor indexes by a conventional organoleptic test.

FIG. 4 is a graph showing that the odor indexes calculated as described above are substitutable for the odor indexes by the conventional organoleptic test. In FIG. 4, the odor indexes by the conventional organoleptic test with respect to the plurality of sample gases belonging to the same category of the odor are placed in a horizontal axis, and the calculate values by the aforementioned regression analysis method are placed on a vertical axis. As clearly understood from FIG. 4, even if the original odor is diluted to a considerably low concentration, both indexes by the conventional organoleptic test and by the analysis of the invention respond to each other with a very good accuracy. Thus, it can be understood that the odor index can be precisely calculated by the method of the invention.

According to the odor measuring apparatus of the invention, the index value, such as the odor index, which was based on the sense of smell of a panel or person, can be measured easily with a good repeatability. Also, unlike the analyzing method using the conventional gas chromatography, an odor may be a compound in which a plurality of materials is mixed. Further, the materials are not required to be the known materials causing the malodor, and even if the materials themselves are unknown, the odor index or the odor intensity can be obtained.

Incidentally, the aforementioned embodiment is one example, and can be freely modified and amended within the gist of the present invention. As the order sensor, a saw device, QCM and MOSFET may be used.

While the invention has been explained with reference to the specific embodiments of the invention, the explanation is illustrative and the invention is limited only by the appended claims.

What is claimed is:

1. An odor measuring apparatus, comprising:

a plurality of detecting means having different characteristics and adapted to contact a sample gas for detecting odor components in the sample gas and providing detection outputs and a pattern of the odor components contained in the sample gas, odor fractionating means electrically connected to the detecting means and having a memory memorizing patterns of the odor components for typical odor categories in advance, said odor fractionating means determining that odor in the sample gas belongs to one of the odor categories memorized in the odor fractionating means based on the pattern of the odor components obtained from the detecting means, and computing means electrically connected to the detecting means and the odor fractionating means and having a memory memorizing regression lines determined in advance for the odor categories, said computing means calculating an index value regarding the odor in the sample gas based on the detection outputs obtained from the detecting means by using one of the regression lines determined in advance for the odor categories.

2. An odor measuring apparatus according to claim 1, wherein said pattern of the odor components includes kinds and amounts of the odor components and is expressed as radar graph.

3. An odor measuring apparatus according to claim 2, wherein said memory in the computing means contains coefficients for each of the plurality of the detecting means in each odor category.

4. An odor measuring apparatus according to claim 1, wherein said computing means memorizes typical index values for the respective odor categories by experiments, and calculates the index value of the sample gas using the typical index values.

5. An odor measuring apparatus according to claim 4, wherein said detecting means is a metal oxide semiconductor sensor or a sensor utilizing a conductive high polymer.

6. An odor measuring apparatus according to claim 4, further comprising a sample gas supply port, and a collecting tube connected to the sample gas supply port and the detecting means, said odor components being obtained at the collecting tube by allowing the sample gas to pass through the collecting tube and then supplied to the detecting means.

7. An odor measuring apparatus according to claim 6, wherein said collecting tube includes a heater to be heated when releasing the odor components in the collecting tube to the detecting means.

8. An odor measuring apparatus according to claim 4, further comprising an analog-to-digital converter for converting the detection outputs from the detecting means into digital values thereof to be used in the odor fractionating means and the computing means.

* * * * *